United States Patent [19]

Morikawa et al.

[11] Patent Number: 4,472,573
[45] Date of Patent: Sep. 18, 1984

[54] NITROSOUREA DERIVATIVE AND PROCESS FOR PREPARING SAME

[75] Inventors: Tamio Morikawa, Tokyo; Kenji Tsujihara, Urawa; Mikio Takeda, Urawa; Yoshihisa Arai, Urawa, all of Japan

[73] Assignee: Tanabe Seiyaku Co., Ltd., Japan

[21] Appl. No.: 358,818

[22] Filed: Mar. 16, 1982

[30] Foreign Application Priority Data

Apr. 2, 1981 [JP]  Japan .................................. 56-50393

[51] Int. Cl.³ ........................................... C07H 11/02
[52] U.S. Cl. ..................................... 536/17.7; 536/4.1
[58] Field of Search ................................. 536/17.7, 22

[56] References Cited

U.S. PATENT DOCUMENTS

| | | | |
|---|---|---|---|
| 3,767,640 | 10/1973 | Suami et al. | 536/17.7 |
| 4,086,415 | 4/1978 | Suami et al. | 536/22 |
| 4,156,777 | 5/1979 | Kimura | 536/22 |
| 4,182,757 | 1/1980 | Tsujihara et al. | 536/22 X |
| 4,273,766 | 6/1981 | Stanek | 536/17.7 |

FOREIGN PATENT DOCUMENTS 2119964 11/1971 Fed. Rep. of Germany ..... 536/17.7
141815 12/1976 Japan .

OTHER PUBLICATIONS

Johnston et al., Journ. Med. Chem. 18 (1), p. 104 (1975).

Primary Examiner—Ethel G. Love
Attorney, Agent, or Firm—Jordan B. Bierman; Linda Bierman

[57] ABSTRACT

A nitrosourea compound of the formula:

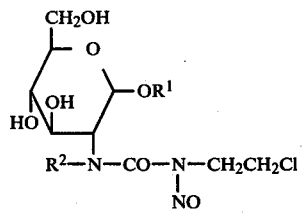

wherein $R^1$ is lower alkyl and $R^2$ is lower alkyl or lower alkoxy-lower alkyl, which may be prepared by nitrosation of a compound of the formula:

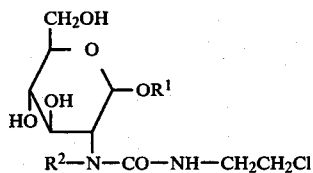

wherein $R^1$ and $R^2$ are the same as defined above. Said nitrosourea compound is useful as an anti-tumor or anti-leukemic agent.

11 Claims, No Drawings

NITROSOUREA DERIVATIVE AND PROCESS FOR PREPARING SAME

This invention relates to a novel nitrosourea derivative and process for preparing same. More particularly, it relates to a compound of the formula:

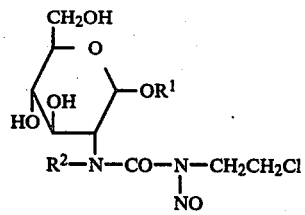
(I)

wherein $R^1$ is lower alkyl and $R^2$ is lower alkyl or lower alkoxy-lower alkyl.

It is known that 1-(2-chloroethyl)-1-nitroso-3-β-(D-mannopyranosyl)urea and 1-(2-chloroethyl)-1-nitroso-3-β-(D-glucopyranosyl)urea (The latter compound being hereinafter referred to as "GANU") increase the life span of mice implanted intraperitoneally with the tumor cells of lymphoid leukemia L-1210 (U.S. Pat. No. 4,086,415). It is also known that 1-(2-chloroethyl)-1-nitroso-3-β-(D-lactosyl)urea and 1-(2-chloroethyl)-1-nitroso-3-β-(D-maltosyl)urea show anti-tumor activity against leukemic cells (Japanese Patent Publication (unexamined) No. 141815/1976).

We have now found that the nitrosourea compound (I) of the present invention shows potent anti-tumor or anti-leukemic activity and is useful to inhibit the growth of malignant tumor cells in mice.

Moreover, the compound (I) may show an excellent therapeutic index estimated in terms of ratio of M.T.D. (the maximum tolerated dose which shows 100% inhibition for the growth of Ehrlich ascites tumor in mice without causing the death of said mice) to M.E.D. (the minimum effective dose which shows 100% inhibition for the growth of said ascites tumor), and have great safety for use as an anti-tumor agent.

In the above-mentioned formula (I), representative examples of the group $R^1$ include lower alkyl such as methyl, ethyl, n-propyl, isopropyl, isobutyl, n-butyl, sec-butyl and t-butyl. On the other hand, representative examples of the group $R^2$ include lower alkyl such as methyl, ethyl, n-propyl, isopropyl, n-butyl, isobutyl, sec-butyl, t-butyl, n-amyl, isoamyl, sec-amyl, and t-amyl; and lower alkoxy-lower alkyl such as methoxymethyl, methoxyethyl, methoxy-n-propyl, methoxy-n-butyl, methoxy-n-pentyl, ethoxymethyl, ethoxyethyl, ethoxy-n-propyl, ethoxy-n-butyl and ethoxy-n-pentyl. Further, among those of the invention, a preferred subgenus includes the compound of the formula (I) in which $R^1$ is methyl, and $R^2$ is methyl, n-propyl, n-butyl, isobutyl or methoxyethyl.

According to the present invention, the nitrosourea compound (I) is prepared by nitrosation of a compound of the formula:

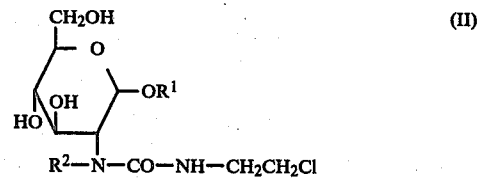
(II)

wherein $R^1$ and $R^2$ are the same as defined above.

The nitrosation reaction is accomplished by contacting the compound (II) with nitrous acid, nitrogen trioxide or nitrogen tetroxide in an inert solvent. The reaction can be preferably carried out at a temperature of $-20°$ to $20°$ C., especially at about $-10°$ to $10°$ C. Water, tetrahydrofuran, acetic acid and formic acid are suitable as the inert solvent. When free nitrous acid is prepared by reacting an alkali metal salt of nitrous acid (e.g., sodium nitrite, potassium nitrite) or a lower alkyl ester thereof (e.g., butyl nitrite, amyl nitrite) with a mineral or organic acid (e.g., hydrochloric acid, sulfuric acid, formic acid or acetic acid), it is preferred that said free nitrous acid is employed for subsequent nitrosation reaction immediately after preparation thereof. On the other hand, when nitrogen trioxide or nitrogen tetroxide is employed in the invention, it is preferred to carry out the nitrosation reaction by dissolving or suspending the starting compound (II) in the inert solvent and then introducing gaseous nitrogen trioxide or tetroxide thereto in presence or absence of an acid acceptor. Sodium bicarbonate, sodium carbonate, potassium carbonate, sodium acetate, potassium acetate are suitable as the acid acceptors.

When the nitrosation reaction is completed, the compound (I) of the invention is readily recovered from the reaction mixture and may be, if required, further purified by silica gel chromatography.

The nitrosourea compound (I) thus obtained shows potent anti-tumor activity against various tumor cells such as Ehrlich's carcinoma, Sarcoma 180, Leukemia L-1210, Lewis lung carcinoma, Yoshida sarcoma and Rat ascites hepatoma. It may be useful to prolong the survival time of mice afflicted with said tumors and/or minimize the growth of said tumors in said animals. It may also be employed for therapy of malignant lymphoma, leukemia, stomach tumor and hepatoma. The nitrosourea compound (I) can be used for pharmaceutical use in the form of a pharmaceutical preparation suitable for either oral or parenteral administration. The compound (I) may also be used in conjunction or admixture with a pharmaceutical excipient. The excipient selected must be the one which does not react with the compound (I). Suitable excipients include, for example, gelatin, lactose, glucose, sodium chloride, starch, magnesium stearate, talcum, vegetable oil and so forth. Other known medicinal excipients may be employed. The pharmaceutical preparation may be a solid dosage form such as, for example, a tablet, a coated tablet, a pill or a capsule; or a liquid dosage form such as, for example, a solution, a suspension or an emulsion. Further, the compound (I) may be employed, for example, in the form of an injection or suppository when administered parenterally. The pharmaceutical preparation may be sterilized and/or may contain auxiliaries such as, for example, preserving and stabilizing agents. The dose of the compound (I) for pharmaceutical use depends on route of administration; the age, weight and condition of the patients; and particular diseases to be treated. In general, it may be used for pharmaceutical use at a dose of 0.3 to 25 mg/kg, especially 0.5 to 15 mg/kg, per day.

Concomitantly, the starting compound (II) of the invention can be prepared by, for example, reacting a lower alkyl-2-amino-2-deoxy-α-D-glucopyranoside with a lower alkyl-aldehyde or a lower alkoxy-aldehyde to give the corresponding schiff base thereof, reducing the schiff base with sodium borohydride to give a lower-2-(lower alkylamino or lower alkoxy-lower alkylamino)-2-deoxy-α-D-glucopyranoside, and then reacting the product with a 2-chloroethyl isocyanate. Moreover, the compound (II) in which $R^2$ is methyl can be prepared by reducing a lower alkyl-2-(N-benzyloxycarbonylamino)-2-deoxy-α-D-glucopyranoside with lithium aluminum hydride, and then reacting the product with 2-chloroethyl isocyanate.

EXPERIMENTS

Chemotherapeutic effects of the nitrosourea compounds of the invention on tumor cells in mice were investigated by the following methods and materials.

METHODS

(A) Preventive Effect Against the Growth of Ehrlich Ascites Tumor $10^6$ tumor cells of Ehrlich ascites carcinoma were inoculated intraperitoneally into a group of five femal mice (ICR mice, body weight: 19–23 g). A test compound was dissolved in a physiological saline solution (In the case where CCNU was employed as the test compound, said compound was suspended in a physiological saline solution containing 0.1% NIKKOL HCO-60 (trademark; a surface active agent manufactured by Nikko Chemicals Co. Ltd.)) and administered intraperitoneally to the mice. The administration of the test compound was begun 24 hours after the inoculation of the tumor cells and performed once a day for 5 days. The volume of ascites in the treated mice were measured after 7 days of the experiment.

(B) Effect on the Life Span of Mice Implanted with Leukemic Cells of L-1210

$10^5$ leukemic cells of L-1210 were inoculated intraperitoneally into a group of four male mice (BDF₁ mice, body weight: 19–23 g). A test compound was dissolved in a physiological saline solution and administered intraperitoneally to the mice. The administration of the test compound was begun 24 hours after the inoculation of the leukemic cells and performed once a day for 5 days. The survival days of the treated mice were observed.

COMPOUND TESTED

| Compound Nos. | Chemical Names |
|---|---|
| | (The compounds of the present invention) |
| 1. | 1-(2-chloroethyl)-1-nitroso-3-n-butyl-3-(methyl α-D-glucopyranosid-2-yl)urea |
| 2. | 1-(2-chloroethyl)-1-nitroso-3-n-propyl-3-(methyl α-D-glucopyranosid-2-yl)urea |
| 3. | 1-(2-chloroethyl)-1-nitroso-3-isobutyl-3-(methyl α-D-glucopyranosid-2-yl)urea |
| 4. | 1-(2-chloroethyl)-1-nitroso-3-(2-methoxyethyl)-3-(methyl α-D-glucopyranosid-2-yl)urea |
| 5. | 1-(2-chloroethyl)-1-nitroso-3-methyl-3-(methyl α-D-glucopyranosid-2-yl)urea |

Known Compounds

CCNU: 1-(2-chloroethyl)-1-nitroso-3-cyclohexylurea
GANU: 1-(2-chloroethyl)-1-nitroso-3-(β-D-glucopyranosyl)urea

RESULTS

The results of the experiments are shown in the following Tables 1 and 2.

TABLE 1

Preventive effect against the growth of Ehrlich ascites carcinoma (Method A).

| Compound Nos. | Dose (mg/kg/day) | Ascites volume[g] T/C[a] | Inhibition ratio[b] (%) | MTD[c] | MED[d] | Therapeutic index[e] |
|---|---|---|---|---|---|---|
| 1. | 200 | — | Toxic (2/5)* | 100 | 1.56 | 64 |
|  | 100 | 0.0/4.1 | 100 | | | |
|  | 25 | 0.0/4.1 | 100 | | | |
|  | 6.25 | 0.0/4.1 | 100 | | | |
|  | 1.56 | 0.0/4.1 | 100 | | | |
|  | 0.78 | 2.7/4.1 | 34.1 | | | |
| 2. | 100 | — | Toxic (2/5)* | 50 | 0.78 | 64 |
|  | 50 | 0.0/4.6 | 100 | | | |
|  | 12.5 | 0.0/4.6 | 100 | | | |
|  | 3.12 | 0.0/4.6 | 100 | | | |
|  | 0.78 | 0.0/4.6 | 100 | | | |
|  | 0.39 | 3.9/4.6 | 15.2 | | | |
| 3. | 100 | — | Toxic (4/5)* | 50 | 0.78 | 64 |
|  | 50 | 0.0/4.6 | 100 | | | |
|  | 12.5 | 0.0/4.6 | 100 | | | |
|  | 3.12 | 0.0/4.6 | 100 | | | |
|  | 0.78 | 0.0/4.6 | 100 | | | |
|  | 0.39 | 2.5/4.6 | 45.7 | | | |
| 4. | 100 | — | Toxic (3/5)* | 50 | 0.39 | 128 |
|  | 50 | 0.0/4.6 | 100 | | | |
|  | 12.5 | 0.0/4.6 | 100 | | | |
|  | 3.12 | 0.0/4.6 | 100 | | | |
|  | 0.78 | 0.0/4.6 | 100 | | | |
|  | 0.39 | 0.0/4.6 | 100 | | | |
|  | 0.19 | 1.4/4.6 | 69.6 | | | |
| 5. | 200 | — | Toxic (5/5)* | 100 | 0.78 | 128 |
|  | 100 | 0.0/4.1 | 100 | | | |
|  | 25 | 0.0/4.1 | 100 | | | |
|  | 6.25 | 0.0/4.1 | 100 | | | |
|  | 1.56 | 0.0/4.1 | 100 | | | |
|  | 0.78 | 0.0/4.1 | 100 | | | |
|  | 0.39 | 3.7/4.1 | 9.8 | | | |
| CCNU | 100 | — | Toxic (5/5)* | 50 | 12.5 | 4 |
|  | 50 | 0.0/5.7 | 100 | | | |
|  | 12.5 | 0.0/5.7 | 100 | | | |
|  | 6.25 | 3.8/5.7 | 33.3 | | | |
|  | 3.12 | 4.5/5.7 | 21.1 | | | |
| GANU | 25 | — | Toxic (5/5)* | 12.5 | 0.39 | 32 |
|  | 12.5 | 0.0/4.8 | 100 | | | |
|  | 3.12 | 0.0/4.8 | 100 | | | |
|  | 0.78 | 0.0/4.8 | 100 | | | |
|  | 0.39 | 0.0/4.8 | 100 | | | |
|  | 0.19 | 1.0/4.8 | 79.2 | | | |
|  | 0.09 | 4.6/4.8 | 4.2 | | | |

Note:
[a]T = the average volume of ascites in the treated mice
C = the average volume of ascites in the untreated mice (control group of mice)
[b]Inhibition ratio (%) = $\frac{C - T}{C} \times 100$
[c]MTD = Maximum Tolerated Dose (i.e., the maximum dose which shows 100% inhibition for the growth of Ehrlich ascites tumor in mice without causing the death of said mice)
[d]MED = Minimum Effective Dose (i.e., the minimum dose which shows 100% inhibition for the growth of said ascites tumor)
[e]Therapeutic index = MTD / MED
*the number of mice died / the number of mice used

TABLE 2

Effect on life span of mice implanted with Leukemia L-1210 (Method B)

| Compound No. | Dose (mg/kg/day) | Mean survival days(T/C)[a] | ILS (%)[b] | 60-day survivors[c] |
|---|---|---|---|---|
| 2. | 50 | >60.0/8.0 | >650.0 | 4/4 |
|  | 25 | >60.0/8.0 | >650.0 | 4/4 |
|  | 12.5 | >37.3/8.0 | >366.3 | 2/4 |
|  | 6.25 | 14.3/8.0 | 78.8 | 0/4 |
| 3. | 50 | >60.0/7.6 | >689.5 | 4/4 |
|  | 25 | >60.0/7.6 | >689.5 | 4/4 |
|  | 12.5 | 16.3/7.6 | 114.9 | 0/4 |
| 4. | 50 | >60.0/8.0 | >650.0 | 4/4 |
|  | 25 | >60.0/8.0 | >650.0 | 4/4 |
|  | 12.5 | >27.5/8.0 | >243.8 | 1/4 |
|  | 6.25 | 15.5/8.0 | 93.8 | 0/4 |

Note:
[a] T = the mean survival days of the treated mice
C = the mean survival days of the untreated mice (control group of mice)
[b] ILS (Increase in Life Span) = $\frac{T-C}{C} \times 100$
[c] 60-day survivors = the number of mice survived for 60 days / the number of mice used Practical and presently-preferred embodiments of the present invention are illustratively shown in the following Examples. Throughout the specification and claims, the term "lower alkyl" and "lower alkoxy" should be interpreted as refering to straight or branched alkyl and alkoxy group having one to five carbon atoms.

EXAMPLE 1

(1) 1.9 g of methyl 2-amino-2-deoxy-α-D-glucopyranoside (cf. J. Chem. Soc., 81 (1957)) are dissolved in 20 ml of methanol, and 0.94 g of n-butylaldehyde is added thereto. The mixture is stirred at room temperature for 5 minutes. Then, 0.6 g of sodium borohydride is added to said mixture, and the mixture is further stirred at room temperature for 2 hours. 20 ml of methanol are added to the reaction mixture, and the mixture is adjusted to pH 4 with concentrated hydrochloric acid. After the mixture is stirred for about 10 minutes, insoluble materials are filtered off and the filtrate is condensed under reduced pressure. 40 ml of methanol are added to the residue, and 1.5 g of 2-chloroethyl isocyanate are added dropwise thereto. The mixture obtained is stirred at room temperature for one hour and then condensed under reduced pressure. The residue thus obtained is purified by silica gel chromatography (solvent; chloroform: benzene: methanol=10: 4: 1). 1.8 g of 1-(2-chloroethyl)-3-n-butyl-3-(methyl α-D-glucopyranosid-2-yl)urea are obtained as colorless powder.

M.p. 55° C. (decomp.) $[\alpha]_D^{25}+87.6°$ (C=0.97, methanol)

(2) 0.90 g of 1-(2-chloroethyl)-3-n-butyl-3-(methyl α-D-glucopyranosid-2-yl)urea is dissolved in 20 ml of tetrahydrofuran, and 0.3 g of anhydrous sodium acetate is added thereto. 1.0 g of nitrogen tetroxide gas is introduced into the mixture at −10° C. for 10 minutes under stirring. The mixture is stirred at same temperature for 10 minutes. 2 ml of methanol are added to the reaction mixture, and said mixture is further stirred for about 10 minutes. After 3 g of anhydrous sodium acetate and 30 ml of ethyl acetate are added to the reaction mixture, 5 ml of water are added thereto at −10° C. and said mixture is stirred for 10 minutes. Then, the mixture is filtered. The filtrate is dried and condensed under reduced pressure. The residue obtained is purified by silica gel chromatography (solvent; ethyl acetate: benzene: methanol=10: 4: 1). 450 mg of 1-(2-chloroethyl)-1-nitroso-3-n-butyl-3-(methyl α-D-glucopyranosid-2-yl)urea are obtained as yellow powder.

M.p. 53° C. (decomp.) $[\alpha]_D^{25}+91.5°$ (C=0.83, methanol) IR $\nu_{max}.^{Nujol}$(cm$^{-1}$): 3400, 1690, 1080, 1020 NMR (d$_6$-DMSO) δ: 0.91 (3H, t, NH—CH$_2$CH$_2$CH$_2$CH$_3$) 3.33 (3H, s, —OCH$_3$), 4.68 (1H, d, J=3 Hz, H−1)

EXAMPLE 2

(1) 1.9 g of methyl 2-amino-2-deoxy-α-D-glucopyranoside, 0.75 g of propionaldehyde, 0.6 g of sodium borohydride and 1.5 g of 2-chloroethyl isocyanate are treated in the same manner as described in Example 1-(1), whereby 1.9 g of 1-(2-chloroethyl)-3-n-propyl-3-(methyl α-D-glucopyranosid-2-yl)urea are obtained as colorless powder.

M.p. 81° C. (decomp.) $[\alpha]_D^{18}+90.5°$ (C=1.16, methanol)

(2) 0.85 g of 1-(2-chloroethyl)-3-n-propyl-3-(methyl α-D-glucopyranosid-2-yl)urea and 1.0 g of nitrogen tetroxide gas are treated in the same manner as described in Example 1-(2), whereby 400 mg of 1-(2-chloroethyl)-1-nitroso-3-n-propyl-3-(methyl α-D-glucopyranosid-2-yl)urea are obtained as yellow powder.

M.p. 67° C. (decomp.) $[\alpha]_D^{17}+91.9°$ (C=1.19, methanol) IR $\nu_{max}.^{Nujol}$(cm$^{-1}$): 3400, 1690, 1080, 1020 NMR (d$_6$-DMSO) δ: 0.83 (3H, t, J=7 Hz, NH—CH$_2$CH$_2$CH$_3$), 1.3-1.8 (2H, m, —NH—CH$_2$CH$_2$CH$_3$), 3.30 (3H, s, —OCH$_3$), 4.62 (1H, d, J=2 Hz, H−1)

EXAMPLE 3

(1) 1.9 g of methyl 2-amino-2-deoxy-α-D-glucopyranoside, 0.94 g of isobutylaldehyde, 0.6 g of sodium borohydride and 1.5 g of 2-chloroethyl isocyanate are treated in the same manner as described in Example 1-(1), whereby 2.0 g of 1-(2-chloroethyl)-3-isobutyl-3-(methyl α-D-glucopyranosid-2-yl)urea are obtained as colorless powder.

M.p. 58° C. (decomp.) $[\alpha]_D^{18}+69.8°$ (C=1.03, methanol)

(2) 0.9 g of 1-(2-chloroethyl)-3-isobutyl-3-(methyl α-D-glucopyranosid-2-yl)urea and 1.0 g of nitrogen tetroxide gas are treated in the same manner as described in Example 1-(2), whereby 400 mg of 1-(2-chloroethyl)-1-nitroso-3-isobutyl-3-(methyl α-D-glucopyranosid-2-yl)urea are obtained as yellow powder.

M.p. 69° C. (decomp.) $[\alpha]_D^{17}+98.8°$ (C=1.03, methanol) IR $\nu_{max}.^{Nujol}$(cm$^{-1}$): 3400, 1695, 1080, 1030 NMR (d$_6$-DMSO) δ: 0.88 (6H, d, J=6.3 Hz, —NH—CH$_2$CH(CH$_3$)$_2$), 3.27 (3H, s, OCH$_3$), 4.63 (1H, d, J=2 Hz, H−1)

EXAMPLE 4

(1) 1.9 g of methyl 2-amino-2-deoxy-α-D-glucopyranoside, 1.2 g of 2-methoxyacetaldehyde, 0.76 g of sodium borohydride and 1.7 g of 2-chloroethyl isocyanate are treated in the same manner as described in Example 1-(1), whereby 2.2 g of 1-(2-chloroethyl)-3-(2-methoxyethyl)-3-(methyl α-D-glucopyranosid-2-yl)urea are obtained as colorless powder.

M.p. 52° C. (decomp.) $[\alpha]_D^{18}+101.2°$ (C=1.13, methanol) (2) 0.90 g of 1-(2-chloroethyl)-3-(2-methoxyethyl)-3-(methyl α-D-glucopyranosid-2-yl)urea and 1.0 g of nitrogen tetroxide gas are treated in the same manner as described in Example 1-(2), whereby 410 mg of 1-(2-chloroethyl)-1-nitroso-3-(2-methoxyethyl)-3-(methyl α-D-glucopyranosid-2-yl)urea are obtained as yellow powder.

M.p 55° C. (decomp.) $[\alpha]_D^{17} + 99.4°$ (C=1.13, methanol) IR $\nu_{max}.^{Nujol}$ (cm$^{-1}$): 3400, 1690, 1095, 1025 NMR (d$_6$-DMSO) δ: 3.22 (3H, s, —OCH$_3$), 3.29 (3H, s, —OCH$_3$), 4.62 (1H, d, J=2 Hz, H—1)

EXAMPLE 5

(1) 3.3 g of methyl 2-(N-benzyloxycarbonylamino)-2-deoxy-α-D-glucopyranoside are dissolved in 100 ml of tetrahydrofuran, and 2.3 g of lithium aluminum hydride are added thereto. The mixture is refluxed for 5 hours under stirring. 15 ml of ethyl acetate are added to the mixture under ice-cooling, and said mixture is refluxed for 10 minutes. After cooling, the mixture is adjusted to pH 2 with 30% sulfuric acid. Insoluble materials are filtered off, and the filtrate is adjusted to pH 8-9 with potassium carbonate. Insoluble materials are again filtered off, and 2 g of 2-chloroethyl isocyanate are added to the filtrate. Then, the mixture is treated in the same manner as described in Example 1-(1), whereby 1.4 g of 1-(2-chloroethyl)-3-methyl-3-(methyl α-D-glucopyranosid-2-yl)urea are obtained as colorless powder.

M.p. 96° C. (decomp.) $[\alpha]_D^{21} + 123.7°$ (C=1.03, methanol)

(2) 0.78 g of 1-(2-chloroethyl)-3-methyl-3-(methyl α-D-glucopyranosid-2-yl)urea and 1.0 g of nitrogen tetroxide gas are treated in the same manner as described in Example 1-(2), whereby 530 mg of 1-(2-chloroethyl)-1-nitroso-3-methyl-3-(methyl αD-glucopyranosid-2-yl)urea are obtained as yellow powder.

M.p. 66° C. (decomp.) $[\alpha]_D^{20} + 149.5°$ (C=1.10, methanol) IR $\nu_{max}.^{Nujol}$ (cm$^{-1}$): 3400, 1690, 1075, 1020 NMR (d$_6$-DMSO) δ: 3.09 (3H, s, —NH—C/$_3$), 3.30 (3H, s, —OCH$_3$), 4.77 (1H, d, J=2 Hz, H—1)

What we claim is:

1. A compound of the formula:

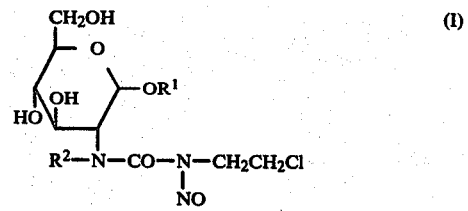

wherein R$^1$ is lower alkyl and R$^2$ is lower alkyl or lower alkoxy-lower alkyl.

2. The compound of claim 1, in which R$^1$ is methyl.

3. The compound of claim 1, in which R$^2$ is methyl, n-propyl, n-butyl, isobutyl or methoxyethyl.

4. The compound of claim 1, in which R$^1$ is methyl, and R$^2$ is methyl, n-propyl, n-butyl, isobutyl or methoxyethyl.

5. The compound of claim 1, in which R$^1$ is methyl, and R$^2$ is n-propyl, isobutyl or methoxyethyl.

6. The compound of claim 1, in which R$^1$ is methyl, and R$^2$ is isobutyl or methoxyethyl.

7. The compound of claim 4, in which R$^1$ is methyl and R$^2$ is methyl.

8. The compound of claim 4, in which R$^1$ is methyl and R$^2$ is n-propyl.

9. The compound of claim 4, in which R$^1$ is methyl and R$^2$ is n-butyl.

10. The compound of claim 4, in which R$^1$ is methyl and R$^2$ is isobutyl.

11. The compound of claim 4, in which R$^1$ is methyl and R$^2$ is methoxyethyl.

* * * * *